US00PP26764P3

(12) United States Plant Patent
Wright et al.

(10) Patent No.: US PP26,764 P3
(45) Date of Patent: May 31, 2016

(54) BLUEBERRY PLANT NAMED 'C05-178'

(50) Latin Name: ***Vaccinium corymbosum* hybrid**
Varietal Denomination: C05-178

(71) Applicants: CostaExchange Pty Ltd., Corindi (AU); Florida Foundation Seed Producers, Inc., Marianna, FL (US)

(72) Inventors: Gary Wright, Corindi Beach (AU); Paul Lyrene, Micanopy, FL (US)

(73) Assignees: CostaExchange Pty Ltd, Corindi (AU); Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 13/999,625

(22) Filed: Mar. 13, 2014

(65) Prior Publication Data

US 2014/0283233 P1 Sep. 18, 2014

Related U.S. Application Data

(60) Provisional application No. 61/851,810, filed on Mar. 13, 2013.

(51) Int. Cl.
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

*Primary Examiner* — Annette Para
(74) *Attorney, Agent, or Firm* — Hahn Loeser & Parks, LLP

(57) ABSTRACT

A new and distinct cultivar of blueberry (*Vaccinium corymbosum* hybrid) plant named 'C05-178,' characterized by its strong growth vigor, semi-upright plant growth habit, mid-season, large fruit size, and fruit with strong firmness and crispy skin.

4 Drawing Sheets

Latin name of the family, genus, and species: Family—Ericaceae. Genus—*Vaccinium.* Species—*corymbosum* hybrid.

Variety denomination: The new blueberry plant claimed is of the variety denominated 'C05-178.'

BACKGROUND OF THE INVENTION

The present invention relates to a new and distinct perennial variety of *Vaccinium corymbosum* hybrid (blueberry), which has been given the variety denomination of 'C05-178.' The new variety 'C05-178' shows distinctive traits such as strong growth vigor, fruit with strong firmness, low chilling requirement. The new variety 'C05-178' is intended for use as fresh fruit for shipping, customer pick and processing markets and as a home garden plant.

The new blueberry cultivar is a selection resulting from seedlings produced in a controlled breeding programme of *Vaccinium* varieties in Florida, USA in 2003 from a cross of the blueberry variety known as 'Early crisp' (seed parent) (unpatented) and the blueberry variety known as 'FL03-061' (pollen parent) (unpatented). The seed from the cross was sown and grown in Corindi Beach, New South Wales, Australia. The new cultivar was discovered and selected in 2005 as a single plant within a population of seedlings resulted from the controlled cross, in an experimental block in the field at Corindi Beach, New South Wales, Australia, and has since been named 'C05-178.' Selection criteria were a combination of strong growth vigor, low chilling requirement and fruit with strong firmness. The new variety was subsequently evaluated for a number of years at the commercial farm at Corindi Beach, New South Wales, Australia.

Asexual reproduction of the new variety 'C05-178' by softwood cutting propagation since 2005 at Corindi Beach, New South Wales, Australia has demonstrated that the new variety reproduces true to type with all of the characteristics, as herein described, firmly fixed and retained through successive generations of such asexual propagation, with the clones phenotypically identical to the original plant.

The seed parent 'Early crisp' is characterized by an early timing of ripening of fruit. The pollen parent 'FL03-061' is characterized by a late to very late timing of ripening of fruit. The new variety 'C05-178' differs from the seed and pollen parents in that 'C05-178' has a mid-season cropping time, ripening after 'Early Crisp' and before 'FL03-061.' The new variety 'C05-178' has maintained its distinguished characteristics throughout successive asexual propagation.

SUMMARY OF THE INVENTION

The new blueberry variety originated from a cross of 'Early crisp' (seed parent) and the variety known as 'FL03-061' (pollen parent) in 2003 Florida, US. The seed parent is characterized by an early timing of ripening of fruit. The pollen parent is characterized by a late to very late timing of ripening of fruit.

The new blueberry variety 'C05-178' resulted from seedlings produced in a controlled breeding program. The cross was made in 2003 in Florida, USA and the seed was sown and grown on in Corindi Beach, NSW, Australia.

The new variety was selected in 2005 from among plants located on land at Corindi Beach and has since been named 'C05-178'. Since then plants of 'C05-178' were propagated by cuttings for further evaluation and resulted to be uniform and stable. Asexual reproduction of the new variety 'C05-178' by cutting propagation since 2005 at Corindi Beach, NSW, Australia, has demonstrated that the new variety reproduces true to type plants.

The new variety was selected in 2005 as a single plant within a population of seedlings resulting from controlled cross of *Vaccinium* varieties. The seedling population was planted in an experimental block in the field at Corindi Beach, NSW, Australia and the selection of the new variety took place in the same block. Selection criteria were a combination of strong growth vigor, semi-upright habit and large fruit with strong firmness. The new variety was subsequently evaluated for a number of years at the commercial farm at Corindi Beach, NSW, Australia.

The following characteristics of the new variety have been repeatedly observed and can be used to distinguish 'C05-178' as a new and distinct variety of *Vaccinium corymbosum* hybrid:

Strong growth vigor
Semi-upright plant growth habit
Mid-season
Large fruit size
Fruit with strong firmness and crispy skin The new variety differs from the female ('Early crisp'—early cropping) and male ('FL03-061'—late to very late cropping) parents in that 'C05-178' has a mid-season cropping timing. The new variety 'C05-178' has maintained its distinguished characteristics through successive asexual propagation. The variety has been repeatedly asexually reproduced through softwood cuttings in NSW, Australia, and the clones are phenotypically identical to the original plant.

BRIEF DESCRIPTION OF THE DRAWINGS

The accompanying photographic illustration shows typical specimens in full color of the foliage and fruit of the new variety 'C05-178.' The colors are as nearly true as is reasonably possible in a color representation of this type.

Figure 1:
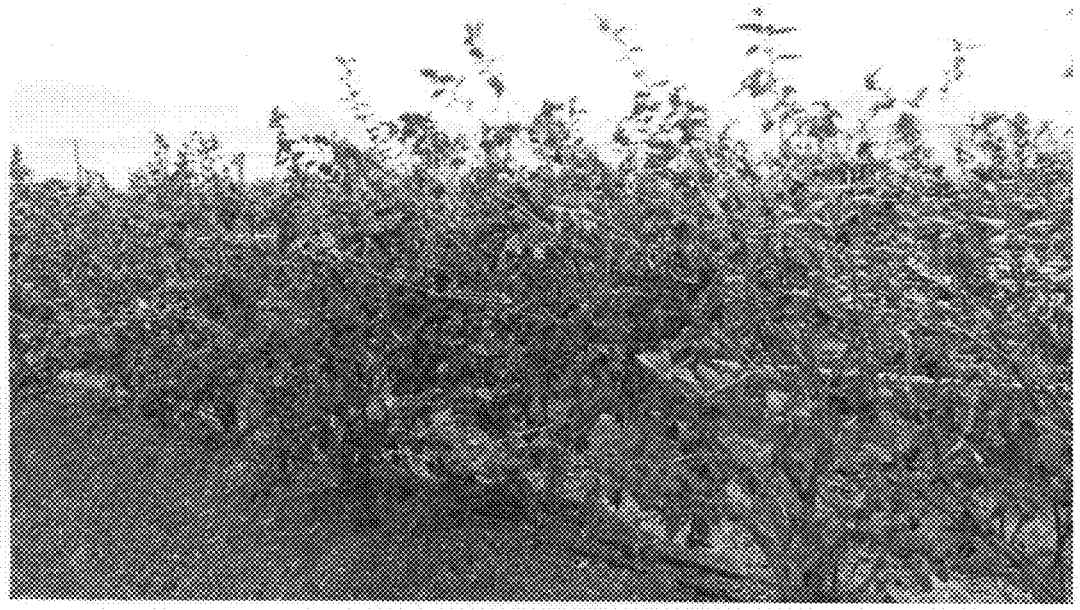
FIG. 1 is a photograph of the new variety 'C05-178,' demonstrating the plant's semi-upright growth habit and the medium leafing during the full crop.
Figure 2:
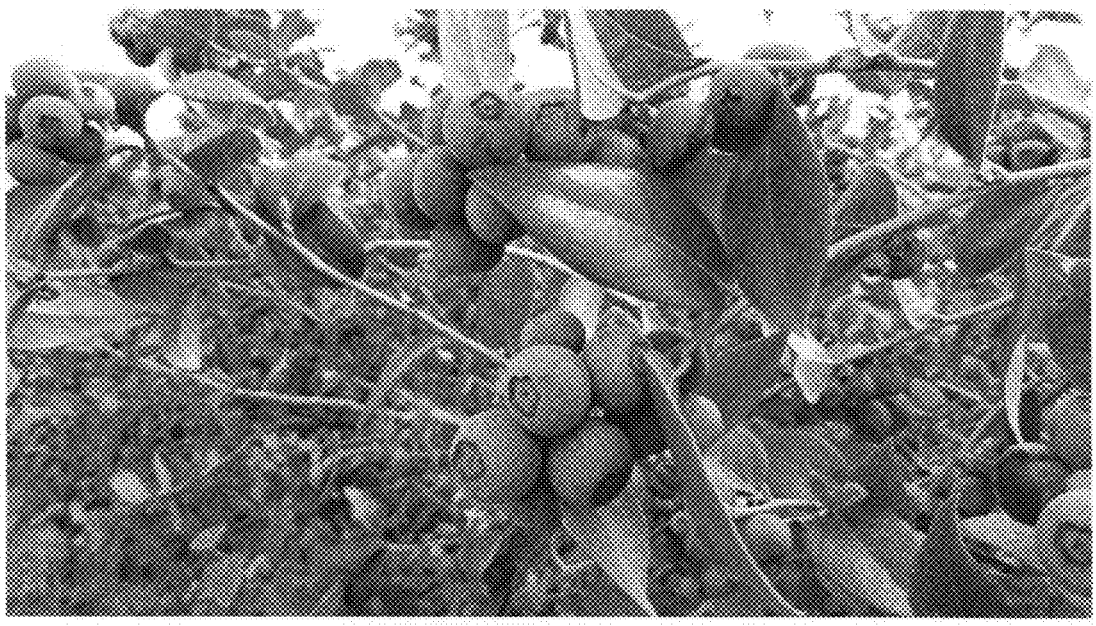
FIG. 2 is a photograph of the fruit of the new variety 'C05-178' compared to that of 'C99-042.'
Figure 3:
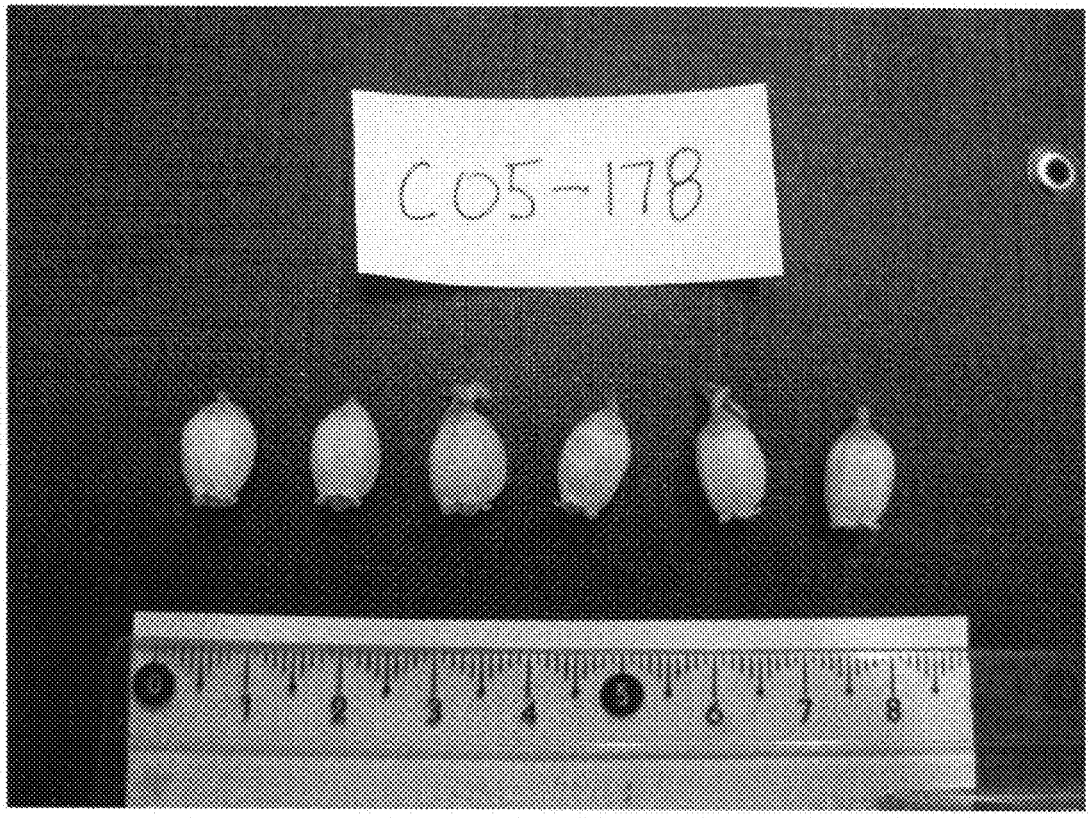
FIG. 3 is a photograph of the flowers of the new variety 'C05-178.'
Figure 4:
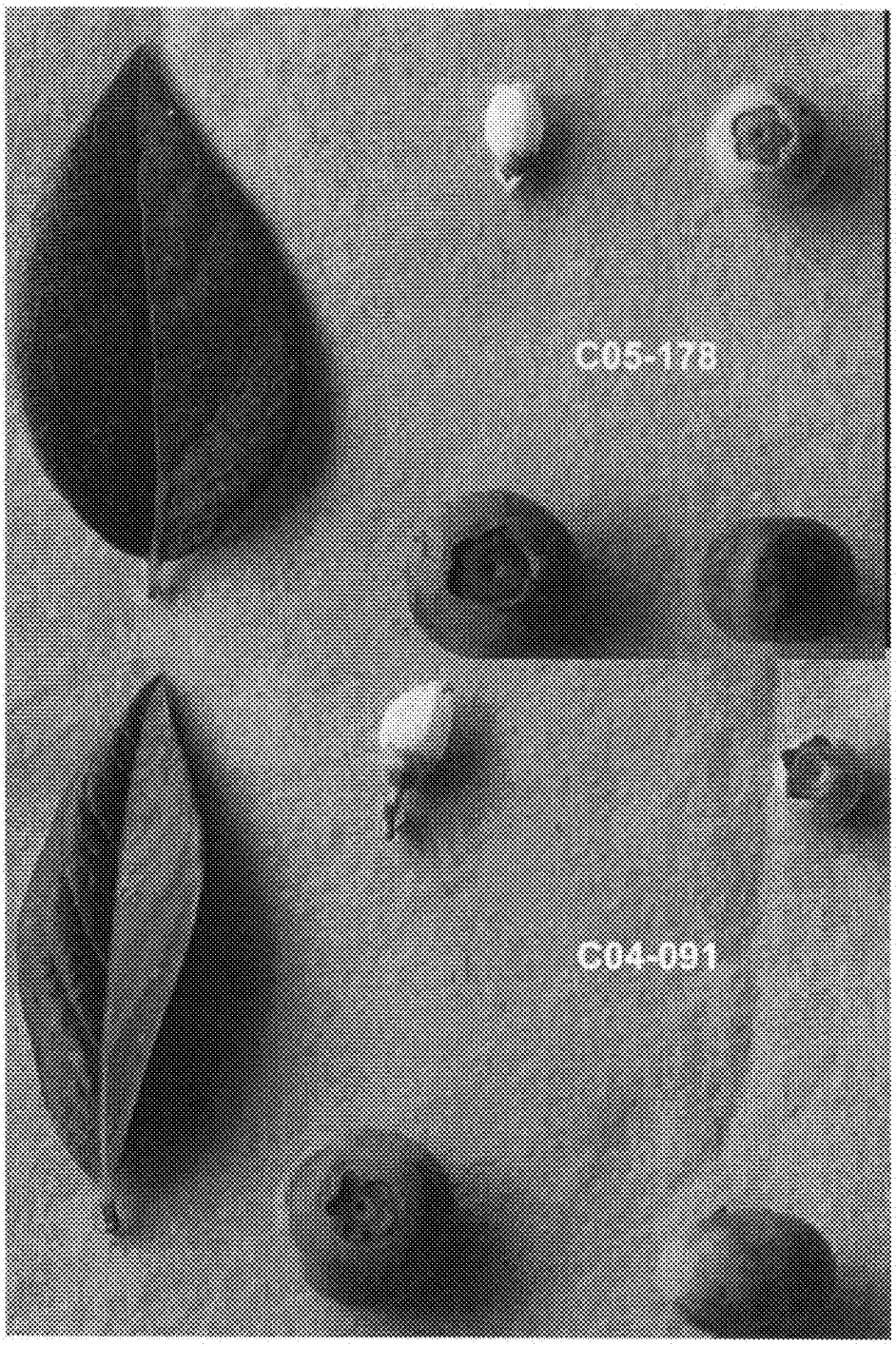
FIG. 4 is a photograph of the new variety 'C05-178,' showing parts of the plant in comparison with the variety 'C04-091.'

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'C05-178.' The data which defines these characteristics was collected from asexual reproductions of the original selection. Dimensions, sizes, colors, and other characteristics are approximations and averages set forth as accurately as possible. The plant history was taken on plants approximately 4 years of age, and the descriptions relate to plants grown in the field in Corindi Beach, New South Wales, Australia. Descriptions of fruit characteristics were made on fruit grown in Corindi Beach, New South Wales, Australia. Color designations are from R.H.S. Chart—edition 2007.

Classification:

*Family*.—Ericaceae.
*Genus*.—*Vaccinium*.
*Species*.—*corymbosum* hybrid.
*Common name*.—Blueberry.

Parentage:

*Seed parent*.—'Early crisp' (unpatented).
*Pollen parent*.—'FL03-061' (unpatented).

Market class: Suitable for the Commercial, Hand Harvest Fresh, Processed, and Home Garden Markets.

PLANT

General:

*Parentage*.—'Early crisp'×'FL03-061'.
*Plant height*.—1.5 m.
*Plant width*.—1.3 m.
*Growth habit*.—Semi-upright, open bush.
*Growth*.—Vigorous.
*Productivity*.—High.
*Cold hardiness*.—Low.
*Cold tolerance*.—Low to medium.
*Chilling requirement*.—Low to medium.
*Tolerance to disease*.—Mild susceptibility to leaf rust.
*Leafing*.—Medium to poor during the summer. The variety retains some leaves during the winter.
*Twigginess*.—Medium to high.

STEM

General:

*Suckering tendency*.—Low.
*Mature cane color*.—Greyed green group 197B.
*Mature cane length*.—0.85 m.
*Mature cane width*.—10.1 mm.
*Bark texture*.—Very smooth.
*Surface texture of new wood*.—Very smooth.
*Internode length on strong, new shoots*.—21.4 mm.
*Fruiting wood*.—36.2 cm in length.

FOLIAGE

General:

*Time of beginning of leaf bud burst*.—Medium to late, around the beginning of September.
*Leaf color* (*top side*).—Near to green group 137A.
*Leaf color* (*under side*).—Green group 137C.
*Leaf arrangement*.—Alternate.
*Leaf shape*.—Elliptic.
*Leaf margins*.—Entire.
*Undulation of margin*.—Very weak.
*Leaf venation*.—Reticulate, vein colour near to yellow-green group 144A.
*Leaf apices*.—Acute.
*Leaf bases*.—Rounded.
*Leaf length*.—61.7 mm.
*Leaf width*.—34.4 mm.
*Leaf length/width ratio*.—1.8.
*Leaf nectarines*.—Absent.
*Pubescence of upper side*.—Absent.
*Pubescence of lower side*.—Absent.
*Cross sectional profile*.—Flat.
*Longitudinal profile*.—Straight.
*Attitude*.—Horizontal.

Petioles:

*Length*.—Average 4.7 mm.
*Width*.—1.7 mm.
*Color*.—Yellow green group 144B.

FLOWERS

General:
*Time of beginning of flowering*.—Medium.
*Time of* 50% *anthesis*.—3rd August.
*Flower shape*.—Urceolate.
*Flower bud density*.—Dense.
*Flower fragrance*.—Little.
*Flower arrangement*.—Alternately.
*Flower type*.—Complete flower, having sepals, petals, stamens and pistils.

Corolla:
*Color*.—White group NN155A.
*Length*.—10.1 mm.
*Width*.—Average 8.3 mm.
*Aperture width*.—5.95 mm.
*Anthocyanin coloration of corolla*.—Absent.
*Corolla ridges*.—Present.
*Protrusion of stigma*.—Absent.
*Shape*.—Urceolate.

Inflorescence:
*Length*.—Ranging between 12 to 17 mm.
*Diameter*.—17 mm.
*Length of peduncle*.—10.3 mm.
*Surface texture of peduncle*.—Smooth.
*Color of peduncle*.—Yellow green group 145C.
*Length of pedicel*.—4.1 mm.
*Surface texture of pedicel*.—Smooth.
*Color of pedicel*.—Yellow green group 145C.
*Number of flowers per cluster*.—10.
*Flower cluster density*.—Dense.

Calyx (with sepals):
*Diameter*.—8.3 mm.

Stamen:
*Length*.—9.4 mm.
*Number per flower*.—10.
*Filament color*.—Yellow-green group 145C.
*Style*.—Length — 9.58 mm.
*Color*.—Yellow-green group N144C.

Pistil:
*Length*.—12.52 mm.
*Ovary color* (*exterior*).—Yellow-green group N144C.

Anther:
*Length*.—4.6 mm.
*Number*.—10.
*Color*.—Greyed-orange group 165B.

Pollen:
*Abundance*.—Medium.
*Color*.—Yellow group 4D.
*Self-compatibility*.—Possible, but smaller fruit sizes (2 g) and very few seeds.

FRUIT

General:
*Time of fruit ripening*.—Mid season.
*Time of* 50% *maturity*.—5th October.
*Fruit development period*.—63 days.
*Cluster density*.—Dense, about 9 berries/cluster.
*Unripe fruit color*.—Yellow-green group 144A.
*Ripe berry color*.—Blue group 103B.
*Berry surface wax abundance*.—Weak to medium.
*Berry flesh color*.—Yellow-green group 145C.
*Berry weight*.—Average 3.2 g.
*Berry height from calyx to scar*.—13.93 mm.
*Berry diameter*.—20.1 mm.
*Berry shape*.—Oblate.
*Fruit stem scar*.—Medium size, dry.
*Sweetness when ripe*.—Medium.
*Firmness when ripe*.—Very firm.
*Acidity when ripe*.—Low.
*Storage quality*.—Excellent.
*Suitability for mechanical harvesting*.—Not suitable.
*Self-fruitfulness*.—High.
*Uses*.—Fresh fruit.

SEED

General:
*Seed abundance in fruit*.—Low (107 seeds in 10 fruit).
*Seed color*.—Greyed-orange group N167A.
*Seed length*.—1.85 mm.

COMPARISON BETWEEN PARENTAL AND COMMERCIAL CULTIVARS

| | Variety | Comparator variety | | | |
|---|---|---|---|---|---|
| Characteristic | C05-178 | C99-042 | Emerald | Star | Snowchaser |
| Soluble solid content (%) | 12.4 | 13.1 | 11.6 | 13.1 | 14.3 |
| Titratable acidity (%) | 0.3 | 0.3 | 0.5 | 0.4 | 0.5 |
| Fruit weight (g) | 3.2 | 1.9 | 3.0 | 1.9 | 1.7 |
| Firmness (g/mm) | 275 | 273 | 187 | 210 | 188 |
| Shelf life (days) | 35 | 23 | 20 | 35 | 25 |
| Leaf length (mm) | 61.7 | 52.5 | 62 | 65.7 | 56.1 |
| Leaf width (mm) | 34.4 | 24.6 | 37 | 27.7 | 32.1 |
| Plant habit | Semi-upright | Semi-upright to spreading | Spreading | Strongly upright to upright | Semi-upright |
| Time of fruit ripening | Mid-season | Early | Mid to late | Late | Very early |

The invention claimed is:

1. A new and distinct variety of blueberry plant named 'C05-178,' substantially as illustrated and described herein.

* * * * *